United States Patent [19]

Bitrolf

[11] 4,202,338
[45] May 13, 1980

[54] DEVICE FOR REMOVING EXCRESCENCES AND POLYPS

[75] Inventor: Ehrenfried Bitrolf, Bretten-Ruit, Fed. Rep. of Germany

[73] Assignee: Richard Wolf GmbH, Knittlengen, Fed. Rep. of Germany

[21] Appl. No.: 959,502

[22] Filed: Nov. 13, 1978

[30] Foreign Application Priority Data

Nov. 18, 1977 [DE] Fed. Rep. of Germany ... 7735281[U]

[51] Int. Cl.² .................... A61B 17/32; A61N 3/00
[52] U.S. Cl. ............................. 128/303.15; 128/320
[58] Field of Search .............. 128/303.14, 303.13, 128/303.15, 303.16, 303.17, 307, 309, 320; 30/116

[56] References Cited

U.S. PATENT DOCUMENTS

| 3,805,791 | 4/1974 | Seuberth et al. | 128/303.14 |
| 3,828,790 | 8/1974 | Curtiss et al. | 128/303.14 |
| 3,955,578 | 5/1976 | Chamness et al. | 128/303.15 |

OTHER PUBLICATIONS

Rokhlin, "Device for Elec. Excision . . . ", Bio. Med. Eng., vol. 8, No. 2, pp. 118-119, Mar./Apr. 1974.

*Primary Examiner*—Lee S. Cohen
*Attorney, Agent, or Firm*—Kinzer, Plyer, Dorn & McEachran

[57] ABSTRACT

A device for removing excrescences and polyps in a body cavity, has a resilient wire loop for fitting around the excresence or polyp, at the distal end of a tubular guide and connectible to a voltage source, the loop being movable by a proximal handle between a position in which the loop is retracted in the guide and an expanded position in which two opposed sides thereof terminate in a distal bulge, one of the sides of the loop having an inwardly kinked proximal portion in front of the distal end of the guide and the other side of the loop having at least two outwardly pointing kinks.

6 Claims, 2 Drawing Figures

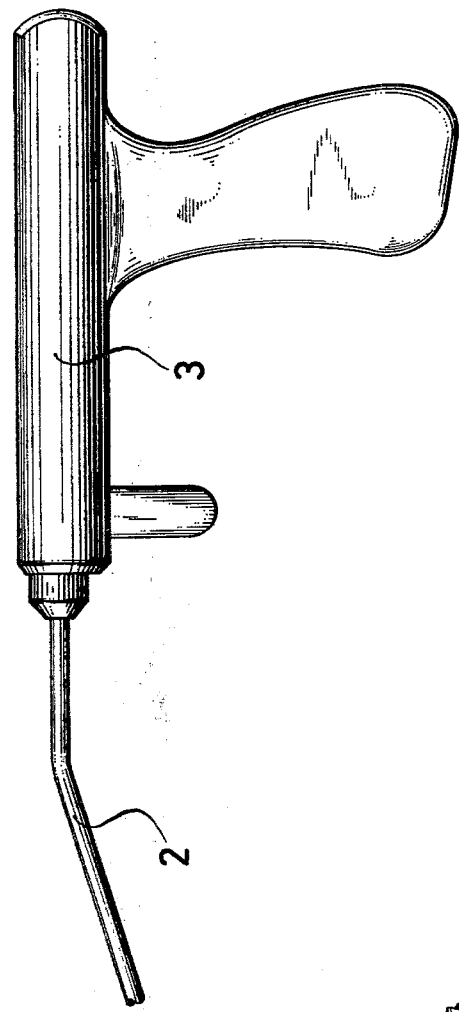
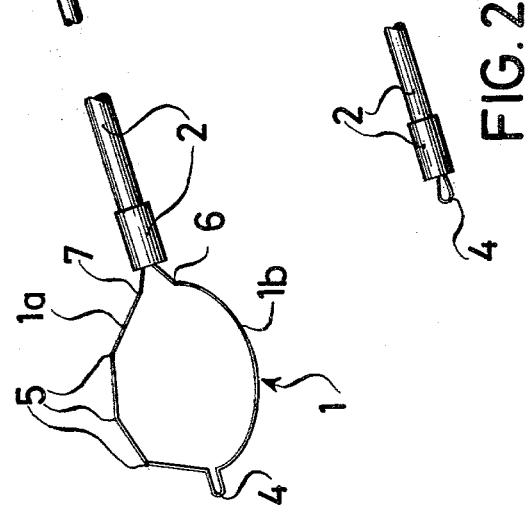

DEVICE FOR REMOVING EXCRESCENCES AND POLYPS

BACKGROUND OF THE INVENTION

1. Field of the Invention

The invention relates to devices for removing excrescences and polyps in body cavities.

2. Description of the Prior Art

One such device which is known to the Applicants, comprises a loop of steel wire for fitting around the excresence or polyp, which is connectible to a voltage source, which opens out resiliently into an oval, whose distal end contains a semi-circular bulge of small radius and which can be drawn into the distal end of a tubular guide by means of a proximal handle at which time the opposite sides of the loop come together.

It has been found that loops of this kind, which are fed with HF current, have only a comparatively short life and that after having been used only one to three times, they frequently fail to open out fully to their original oval shape when extended from their tubular guide and thus can no longer be fitted round a polyp or excrescence.

The main object of the innovation is therefore substantially to lengthen the life of such loops in devices for removing excrescences and polyps.

SUMMARY OF THE INVENTION

To this end, the present invention consists in a device for removing excrescences and polyps which comprises a loop of steel wire which can be connected to a voltage source, which opens out resiliently into an oval, whose distal end contains a semi-circular bulge of small radius, and which can be drawn into the distal end of a tubular guide by means of a proximal handle, at which time the sides of the loop come together, characterised in that one side of the loop, which loop is extended from the guide and opens out in an oval, is kinked inwards in its proximal portion in front of the distal end of the guide, and the other side of the loop has at least two and advantageously three outward pointing kinks.

The inwardly pointing kink in one side of the loop on the one hand makes it easier to draw the loop into the tubular guide or guide-sleeve and on the other hand creates a pronounced set in this side towards an oval, outcurving configuration, and what is achieved by the kinks in the other side of the loop is that this side continues to assume its original substantially oval curvature when extended even after frequent use, since the outwardly pointing kinks assist in resiliently expanding the loop.

To make retraction into the guide even easier, the side of the loop which is provided with at least two kinks may also be provided in its proximal portion with an inward pointing kink.

In a preferred embodiment of the invention, the portions of the one side of the loop in front of, between and behind the kinks are substantially straight portions of wire whose length is equal or approximately equal.

BRIEF DESCRIPTION OF THE DRAWINGS

FIG. 1 is a side view of a device for removing excrescences and polyps, showing an actuating handle, a guide, and a wire loop in an extended position, the guide being broken away intermediate its ends and the distal end of the guide and the loop being to a larger scale, and FIG. 2 shows the distal end of the guide and wire loop to the same larger scale as in FIG. 1, with the wire loop in a retracted, drawn in, position.

DESCRIPTION OF THE PREFERRED EMBODIMENT

The device for removing excrescences and polyps in body cavities by means of HF current comprises a loop 1 of spring-steel wire from which lengths of wire run through a tubular guide 2 to a handle 3 which is actuable from its proximal end and the lengths of wire constitute conductors which can be connected to a source HF voltage which is not shown. Since the structure of the actuating handle and the guide, and the source of HF voltage are, in themselves, well known they have not been described in detail. To allow the wire loop 1 to be introduced into a body cavity through a trocar sleeve or the instrument inserting passage of an endoscope, the loop is drawn or retracted into the distal end of the guide by means of the handle, and it is then extended (expanded) in the body cavity to fit round a polyp. The loop 1 terminates distally in a semi-circular bulge 4 of small radius.

To ensure that when extended the loop will consistently, that is to say after having been used many times, open out or expand again to its full original oval shape by its natural resilience to allow it to be fitted round a polyp, one side 1a of the loop 1 is provided at three points with outward pointing or directed kinks 5, the lengths of wire between the kinks and in front of and behind the kinks being substantially straight and advantageously of the same or approximately the same length.

The other side 1b of the loop remains of substantially the known half-oval (arcuate) shape but its proximal portion in front of the distal end of the guide 2 is provided with an inward pointing or directed kink 6. A kink 7 of this kind, although less pronounced, may also be provided in the other side 1a of the loop. The kinks 6 and 7 on the one hand make it easier to draw the loop 1 into the guide 2 but on the other hand they also assist the action of the sides 1a, 1b of the loop as they expand into an oval.

Various modifications may be made without departing from the scope of the invention as defined in the appended claims. For example instead of three outwardly pointing kinks 5 the side 1a of the loop 1 may have two outwardly pointing kinks.

I claim:

1. A device for removing excrescenses and polyps in a body cavity, comprising:
   (a) a tubular guide having proximal and distal ends,
   (b) a resilient wire loop for fitting around an excrescense or polyp, at the distal end of the guide and of generally oval configuration in an expanded position thereof,
   (c) an actuating handle at the proximal end of the guide connected to said loop, for moving said loop between said expanded position and a position in which said loop is retracted in the distal end of the guide, and
   (d) means for connecting said loop to a voltage source,
   (e) said loop having, as considered in its expanded position,
      (i) a small bulge at one end,
      (ii) two opposed sides extending from said bulge towards said distal end of the guide, of which one side is of generally arcuate form, (iii) an inwardly kinked proximal portion in said one of said two sides, in front of the distal end of the guide, and (iv) at least two outwardly pointing kinks in the the other of said two sides.

2. A device as claimed in claim 1, wherein said other of said two sides of the loop has a slightly inwardly kinked portion in front of the distal end of the guide.

3. A device as claimed in claim 2, wherein said other side of the loop has substantially straight portions in front of, between and behind the outwardly pointing kinks.

4. A device as claimed in claim 3, wherein the straight portions have lengths which are at least substantially equal.

5. A device as claimed in claim 1, wherein said other side of the loop has substantially straight portions in front of, between and behind the outwardly pointing kinks.

6. A device as claimed in claim 5, wherein the straight portions have lengths which are at least substantially equal.

* * * * *